United States Patent
Gonzalez-Gonzalez

(10) Patent No.: US 9,936,705 B2
(45) Date of Patent: Apr. 10, 2018

(54) BIOCIDE FORMULATION FOR PROTECTING THE SKIN, COMPRISING PENTAHYDRATE COPPER SALTS AND HEPTAHYDRATE ZINC SALTS

(71) Applicant: BIOGENESIS ANIMAL HEALTH, Osorno (CL)

(72) Inventor: Jorge Luis Gonzalez-Gonzalez, Osorno (CL)

(73) Assignee: BIOGENESIS ANIMAL HEALTH, Osorno (CL)

( * ) Notice: Subject to any disclaimer, the term of this patent is extended or adjusted under 35 U.S.C. 154(b) by 0 days.

(21) Appl. No.: 14/892,885

(22) PCT Filed: Jun. 11, 2015

(86) PCT No.: PCT/CL2015/050017
§ 371 (c)(1),
(2) Date: Jul. 13, 2016

(87) PCT Pub. No.: WO2015/192260
PCT Pub. Date: Dec. 23, 2015

(65) Prior Publication Data
US 2016/0316758 A1 Nov. 3, 2016

(30) Foreign Application Priority Data
Jun. 16, 2014 (CL) .................................. 1582-2014

(51) Int. Cl.
| A61K 33/32 | (2006.01) |
| A61K 33/34 | (2006.01) |
| A61K 31/28 | (2006.01) |
| A61K 31/315 | (2006.01) |
| A61K 31/30 | (2006.01) |
| A23K 1/18 | (2006.01) |
| A01K 29/00 | (2006.01) |
| A01N 59/20 | (2006.01) |
| A01N 25/02 | (2006.01) |
| A61K 33/30 | (2006.01) |
| A01N 59/16 | (2006.01) |

(52) U.S. Cl.
CPC ............ *A01N 59/20* (2013.01); *A01N 25/02* (2013.01); *A01N 59/16* (2013.01); *A61K 33/30* (2013.01); *A61K 33/34* (2013.01)

(58) Field of Classification Search
None
See application file for complete search history.

(56) References Cited

U.S. PATENT DOCUMENTS

| 5,696,169 A | 12/1997 | Otsu et al. |
| 6,183,785 B1 | 2/2001 | Westfall |
| 2004/0058011 A1 | 3/2004 | Petersson et al. |
| 2007/0224230 A1 | 9/2007 | Fabre et al. |
| 2010/0284951 A1 | 11/2010 | Pongprapansiri et al. |

FOREIGN PATENT DOCUMENTS

| CL | 1774-2012 | 10/2012 |
| CL | 3434-2012 | 5/2013 |
| EP | 2724724 | 4/2014 |
| WO | 2009055799 | 4/2009 |

OTHER PUBLICATIONS

CL 1774-2012 machine translation; created Sep. 6, 2016.*
CL 1774-2012 (full document).*
Pedtrace; published (Dec. 8, 2004) on RxList (http://www.rxlist.com/pedtrace-drug.htm); downloaded Mar. 16, 2017.*
Holzhauer, et al., "Curative effect of topical treatment of digital dermatitis with a gel containing activated copper and zinc chelate", Veterinary Record, Nov. 19, 2011 (5 pages).
International Search Report, dated Sep. 22, 2015, PCT/CL2015/050017 (7 pages).

* cited by examiner

*Primary Examiner* — Jeffrey T. Palenik
(74) *Attorney, Agent, or Firm* — Hamre, Schumann, Mueller & Larson, P.C.

(57) ABSTRACT

The present invention is related to a biocide formulation to protect, prevent or treat skin infections in a combination of pentahydrate copper salts and heptahydrate zinc salts as active biocide compounds. Preferably, the copper salt is pentahydrate copper salt and the zinc salt is heptahydrate zinc salt. In a preferred realization, the formulation comprises agents to enhance adhesion to the skin. In another preferred realization of the invention, the formulation is suitable to be applied to the teats or udders of the milking animals, inter milking, for the treatment and prevention of mastitis.

19 Claims, 3 Drawing Sheets

BIOCIDE FORMULATION FOR PROTECTING THE SKIN, COMPRISING PENTAHYDRATE COPPER SALTS AND HEPTAHYDRATE ZINC SALTS

TECHNICAL FIELD

This invention belongs to the field of dermatological formulations of clinical use in mammals.

Particularly, the present invention provides a broad spectrum biocide composition or formulation to protect the skin, preventing or treating skin infections, in a combination of pentahydrate copper salts and heptahydrate zinc salts as active biocide compounds.

In a preferred realization, the formulation includes plasticizers and emollients in order to improve adhesion to the skin.

In another preferred realization of the invention, a formulation being useful in the milk production industry for its use in the prevention and/or treatment of mastitis in milking animals.

PREVIOUS INFORMATION

Bovine mastitis is an inflammatory disease of the mammary gland and represents one of the main economic and productive problems faced by the milking industry worldwide. The high costs associated with this disease derive from its impact on the animal health and welfare and on the profitability of sales due to the impact on production and the quality of milk.

Annual losses include the cost of treatment with antibiotics, veterinary care, elimination and losses in the production of milk.

Bovine mastitis is a disease starting with the invasion and colonization of microorganisms through the hole of the teat duct that causes the mammary gland to become swollen resulting in physical and chemical changes to the milk.

Bacteria are the main microorganisms involved, especially *S. aureus, E. coli* and *Streptococcus uberis* among others.

Intramammary infections cause two states of bovine mastitis: clinical and subclinical. The clinical manifestation characterizes for clinical alterations of the gland and/or the milk expressing in organoleptic changes (formation of clots and yellow color). In the subclinical mastitis, the visual symptoms are absent, but the samples of milk present a high count of somatic cells. Thus, according to Schukken, the bovine mastitis is defined when the count of somatic cells is higher than 200,000 cells by milliliter, reducing the commercial value of milk.

The classic techniques for the control of mastitis include different strategies, such as treating the cow after the breast-feeding period ends, milking techniques, disinfection of teats with topical antiseptic substances (pre-immersion and immersion) and treatment of clinical mastitis with antibiotics.

It is well-known that cows' teat skin is permanently exposed to environmental contamination; in the first place, due to the handling of milk producing cows, i.e. cows that pasture and sleep in the same barns they contaminate with urine and fecal matter.

Another form of contamination is the actual milking place (milking rooms); here, there is high contamination exposure through the milking equipment, especially milking cups, which are in direct contact with the teat skin; towels used to prepare cows before milking, i.e. teats are dried before placing the milking units; and the milkers' hands, all these elements are important cross contamination vectors among the animals. Therefore, it is necessary to protect teats after completing the milking process, which lasts 5 to 6 minutes, approximately, by applying a disinfectant product. In the state of the art there are many disinfectant products, especially formulated for teats or udders, and known as "teat dipping". Many of these products are iodine-base compounds, i.e. they use an iodized disinfectant in solutions from 7000 to 10000 ppm iodine.

Spite the use of this iodized solution as disinfectant, cows are contaminated and infected, a fact that occurs after milking, when the teat sphincter is still open due to the suction effect caused by the milk cup to extract milk. The bovine mastitis is still a problem all over the world for the milk industry.

This space, formed in the teat duct, makes contamination very common, especially when the disinfectant used losses effectiveness when it becomes inactive in the presence of organic matter, as in the case of iodized compounds. Therefore, it is necessary to improve the quality of the disinfectant solution used in order to protect the teat against infections, as the solution should have a high biocide power in order to eliminate all bacteria and micro-organisms present in the teat skin, not being inactivated in the presence of organic matter, and continue to be active on the teat skin until the next milking. Effectiveness should be given by adherence to skin and by the active compound activity. Bad adherence may cause the product to run off the skin, losing all its effectiveness due to a mechanical defect, in this case.

The present invention is given in the context of seeking a solution to this specific technical problem.

STATE OF THE ART

As indicated above, there are many products in the market to apply to teats, based on iodine and chlorhexidine. However, these products present many limitations, which make it necessary to seek new alternatives to solve this technical problem. For instance, iodine-based products are irritating and dry the skin, and their continuous use could result in teat wounds and bleeding, although with no infection. On the other hand, both iodine and chlorhexidine products are inactivated in the presence of organic matter and lose their effectiveness.

Inventors have studied this technical problem for a long time, which led them to develop a first biocide product to protect the skin, based on copper salts. The product is protected by application CL 1774-2012. This product has the advantage of not becoming inactivated in the presence or organic matter, and it does not irritate the skin, although its biocide power is not very high, and there are diseases that are resistant to treatment with this product.

In the state of the art, we may also find a compound to treat skin conditions based on copper oxide and zinc oxide, which is described in application CL 3434-2012. Oxides used in the said compound are not water soluble, and it cannot be anticipated that non water soluble compounds' properties, used as particle dispersion, may anticipate the result obtained with water soluble salts of the same elements. For application on animals' teats, it is indispensable for the formulation to be a fluid, so that the teat may be submerged in it and then dry forming a covering film. In order to achieve this, it is indispensable for compounds to be water soluble, which does not happen with the formulation described in CL 3434-2012, where the product obtained is a cream, not a liquid formulation.

Document US2004058011 (PETERSSON LENNART G) of Mar. 25, 2004, refers to a formulation for teat treatment between milking, which contains chlorhexidine combined with non-water soluble zinc compounds; see paragraph 11: "Zinc is present in the form of material containing zinc, particulate, finely divided, selected from the group formed by zinc stearate, zinc chloride, zinc nitrate, zinc oleate, zinc oxide, zinc phosphate, zinc peroxide, zinc iodide, elemental zinc, and mixes of them".

DETAILED DESCRIPTION OF THE INVENTION

Figure 1:
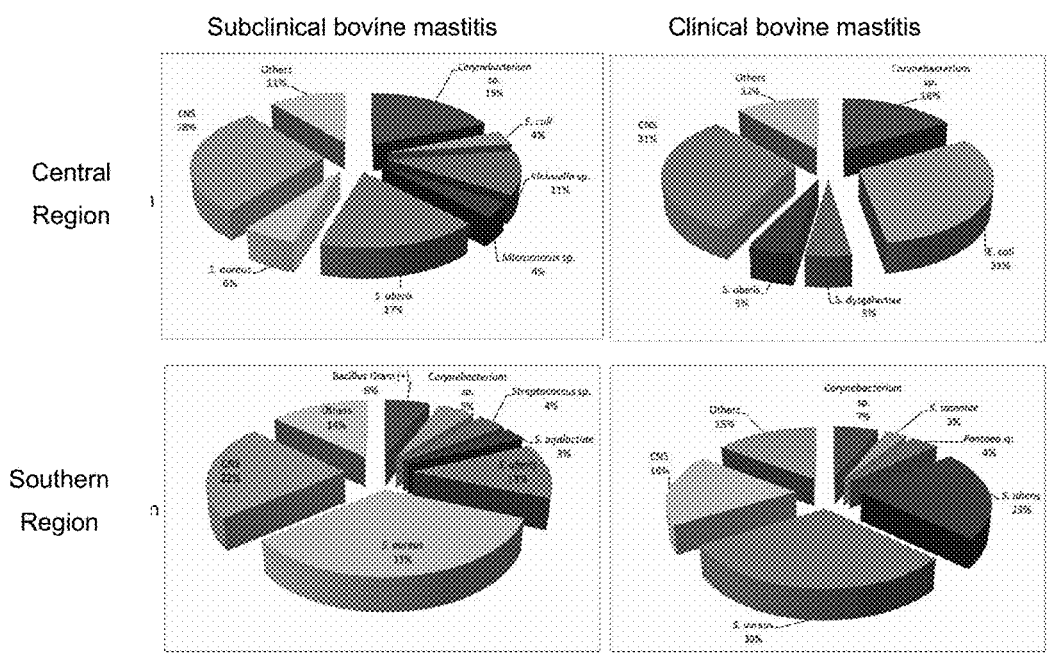
FIG. 1. Distribution of bacterial species isolated from milk samples. 53 and 43 isolates identified from clinical and subclinical mastitis are shown from the Central Region, respectively. In the South Region, 174 and 93 isolates of clinical and subclinical mastitis were identified, respectively. Others include microorganisms frequently isolated ≤2%.

The invention refers to a biocide formulation useful to protect the skin from bacterial infections, and includes the combination of two active biocide compounds, pentahydrate copper salts, and heptahydrate zinc salts.

The antibacterial effect of copper is as a favorable alternative to prevent mastitis, among other skin diseases, strengthened by the joint use of zinc.

For the biocide power to be enhanced and the properties of not becoming inactive with organic matters and not irritating the skin to be kept, the inventors developed the composition of the invention comprising 0.01 to 10% of pentahydrate copper salts, and 0.01 to 10% of heptahydrate zinc salts. As seen in the example 3 of this specification, the new composition achieves unexpected results by totally controlling bacterial infections and eliminating all bacteria present in the udders, so that bacteria are not found in the milk yield.

According to the above, it is shown that the invention has not been anticipated in the previous state of the art.

In addition, without doubt the preferred application of the invention is over the teats of the milking animals to prevent or treat skin infections. Notwithstanding, as actually shown, the invention formulation has important biocide properties; thus it is useful to prevent or treat skin infections of any kind in any animal, even the human being.

Due to the biocide characteristics of active compounds, the invention formulation is useful to prevent or treat any kind of skin infection, whether bacterial, viral or fungal.

Inventors have discovered that the combination of these water soluble copper and zinc salts allow controlling persisting skin pathogen infections.

In a preferred realization, the invention formulation is used as a bath for milking animals' udders, inter-milking, being effective in the treatment and prevention of udder infections.

Notwithstanding this preferred realization, the invention formulation may be applied on any type of skin to be protected from infection, bacterial, fungal, or viral. The invention formulation may be applied to prevent or treat any skin infection.

Preferably, pentahydrate copper salts correspond to pentahydrate copper sulphate, and heptahydrate zinc salts correspond to heptahydrate zinc sulphate.

Considering the invention compounds combination high biocide properties, it is possible to obtain effective biocide formulations with very low concentrations of both compounds, pentahydrate copper salts, and heptahydrate zinc salts.

Preferably, the invention formulation has from 0.01 to 2% pentahydrate copper salts and from 0.01 to 2% heptahydrate zinc salts. Notwithstanding the above, it is possible to obtain more concentrated formulations of both salts in order to facilitate the formulation transportation or for punctual applications on refractory infections, where these concentrated formulations are also within this invention scope. Concentrate formulations could contain from 2 to 10% or more of each one of the compounds; therefore, the invention scope is between 0.01 and 10% pentahydrate copper salts and between 0.01 to 10% heptahydrate zinc salts.

In a preferred invention formulation ready to be applied on the skin, it includes from 0.05 to 1% pentahydrate copper salts and from 0.05 to 1% heptahydrate zinc salts. And, in an especially preferred realization, the invention formulation, easy to be applied on the skin, includes 0.2 to 0.4% of pentahydrate copper salts, and from 0.05 to 3% heptahydrate zinc salts.

The invention formulation is of an aqueous nature, considering the active components' water soluble condition. This way, the formulation solvent is preferably water, but any hydrophilic solvent compatible with the skin may be used.

Furthermore, the invention formulation includes formulation excipients, which are selected from among viscosity modifiers, humectants, emollients, plasticizers, and colorants. These excipients shall be selected from those available in state of the art at the time of the invention realization. Notwithstanding the above, the following are the preferred excipients.

As viscosity modifier or thickener, Xanthan gum is preferred, which represents between 0.2 and 2% of the composition. As emollient and humectant glycerin, sorbitol, propylene glycol, polyethylene glycol, aloe vera, lanolin, and their mixtures are preferred, with emollients and humectants representing from 5 to 30% of the compound. Especially, the composition contains glycerin, which represents from 5 to 12% of the compound. Additionally, in a preferred way, the compound includes sorbitol, which represents from 3 to 10% of it.

In the event the formulation is a compound for udder treatment between milking, it is important that it should contain a plasticizer that allows the compound to adhere to the teat skin. Polyvinyl alcohol is particularly preferred as plasticizer, and it represents from 3 to 10% of the compound, preferably from 5 to 8% of the compound.

The colorant purpose is just visually identify the compound application. The colorant represents from 0.01 to 0.5% of the compound. Any colorant compatible with the skin is appropriate; however, in a preferred realization, a colorant of acceptable level is preferred as food additive, such as Allura colorant.

The invention formulation is useful to prepare a medicine suitable to prevent or treat skin infections. The infection treatment or prevention is through direct application of the medicine containing the invention formulation on the skin area to be protected, repeatedly and in intervals of hours or days, during the time the skin is to be protected and/or until the infection has disappeared.

In a realization, the invention formulation is used to cover, between milking, the teat skin of the animal being milked. After milking the animal, the teat is submerged in the invention formulation and this is let to dry, forming a protective film on the teat. In this case, the formulation includes polyvinyl alcohol or other plasticizer, which forms a polymeric layer on the skin, granting better protection and the permanence of the biocide active components on the skin. The formulation viscosity is also important because, in the event it is too liquid, it will run off before forming the polymeric layer, and would not adhere properly; therefore, when the formulation is used to treat milking animals' teats, it is thickened with Xanthan gum or other viscosity modifier. When using the invention preferred realizations, forming of a film on the teat skin takes from 1 to 2 minutes in order to fully seal it. This sealing remains for more than 12 hours, which is the usual period between milking. Before the next milking, the operator washes the compound off the teat, so that it would not go into the milk. This way, udder mastitis is prevented or treated on milking animals' udders.

Surprisingly, it has been found that the invention formulation allows treating normally persistent udder infections, such as those caused by *Staphylococcus aureus, Streptococcus uberis, Nocardia* Sp., highly prevalent and hard to control. Naturally, the invention formulation is also useful in the prevention and treatment of infections caused by all other existing pathogens, such as *Streptococcus agalactiae, Streptococcus bovis, Streptococcus dysagalactiae, Streptococcus* spp., negative *Staphylococcus coagulase, Escherichia coli*, or other.

According to susceptibility tests made, a concentration as low as 0.5 mg/L of the composition or formulation according to the present invention is able to inhibit the growth of different bacterial species, including those isolated from clinical and subclinical mastitis. In this last case, the formulation showed higher frequencies, even for antibiotic resistant strains, such as neomycin, gentamicin and cefotaxime.

The following are illustrative examples of some of the invention preferred realizations.

EXAMPLES

Example 1: A Formulation Preparation According to the Invention

In order to prepare one of the invention formulations, work was performed on a food grade stainless steel reactor with permanent agitation at 1.5 rpm in a thermal-regulated bath at a temperature between 50 and 60° C. In this case, work was at 60° C. All concentrations are expressed as weight volume percentages with regard to the solution or formulation obtained.

The process is carried out in two stages. In the first stage, the process is started with 100 liters demineralized water at 60° C., as indicated. Slowly, 0.35% pentahydrate copper sulphate salt; 0.15% heptahydrate zinc sulphate, 0.03% Allura colorant, and 0.4% Xanthan gum are added, making sure that no lumps are formed. This mix is kept in agitation at 1.5 rpm for 30 minutes.

In the second stage, temperature is kept at 60° C. and agitation at 1.5 rpm; first, 6% polyvinyl alcohol is slowly added to the previous mix, not to form lumps, then 8% usp glycerin is added, and finally 5% sorbitol. Once all the formulation components are mixed, this is homogenized by keeping the mixture at the same temperature and rpm agitation during 2.5 hours. This gives stability to the formulation, which is ready to be packaged.

The invention formulation composition obtained in this example is summarized in the following Table 1.

TABLE 1

Example of a formulation composition according to the present invention

| Component | Weight/volume % |
|---|---|
| Pentahydrate copper sulphate | 0.35% |
| Heptahydrate zinc sulphate | 0.15% |
| Xanthan gum | 0.4% |
| Usp glycerin | 8% |
| Sorbitol | 5% |
| Polyvinyl alcohol | 6% |
| Allura colorant | 0.03% |
| Csp demineralized water | 100% |

Example 2: Synergism Among the Invention Compound Components

In order to demonstrate one of the invention compound advantages, a bacteria growth inhibition test was performed on plates, or antibiogram, with the most common bacterial infections in milking animals' udder skin. For this, colonies of *Staphylococcus aureus, Streptococcus uberis*, and *Nocardia* Sp. were separately planted in agar plates with PCA culture means, non-selective means, in order to have the bacteria growth on the entire Petri surface plate. 3 plates were planted for each bacteria. Later, in the center of each plate, a paper circle impregnated with the biocide compound to be analyzed was placed. Following, all plates were incubated at 37° C. for 24 hours. In each case, the inhibition halo was measured; results are shown in Table 2.

TABLE 2

Inhibition Halo for Each Active Biocide Component

| Bacteria | Iodine (7000 ppm) | Cu (5000 ppm) | Cu (3500 ppm) + Zn (1500 ppm) |
|---|---|---|---|
| *Staphylococcus aureus* | 2.0 cm | 2.4 cm | 3.2 cm |
| *Streptococcus uberis* | 1.7 cm | 2.3 cm | 2.8 cm |
| *Nocardia* Sp. | 1.3 cm | 2.6 cm | 3.0 cm |

As clearly appreciated in the results, the invention compound clearly shows an advantage over the assessed alternative compounds, being the copper and zinc mixture better than the simple use of copper, and much better than the currently most used biocide compound, iodine.

Example 3: Field Test

The invention formulation obtained in Example 1 was applied as udder protection between milking to a group of 100 cows, which had previously received two different treatments. The herd had been treated with an iodine-base commercial compound for years, which shall be considered as the initial conditions because, spite the treatment, there was a high presence of bacteria in the milk and a high degree of infections in udders. Later, the herd was treated with a compound property of the inventors, protected in patent CL 1774-2012, which only contains pentahydrate copper sulphate as active compound, and whose formulation is summarized in Table 3.

TABLE 3

Example of formulation composition

| Component | Weight/volume % |
|---|---|
| Pentahydrate copper sulphate | 0.5% |
| Lanolin | 2% |
| Xanthan gum | 0.3% |
| Usp glycerin | 6% |
| Colorant | 1% |
| Demineralized water | 90.2% |

The herd was treated during one month approximately with the compound in Table 3, and an important pathogen and somatic cell reduction was observed in the milk tank. However, the inventors observed that some infections were refractory to treatment, as they persisted after one month (31 days) daily application. For this reason, the new invention compound was developed, which was applied to the same herd during 25 days, as udder protection between milking.

After the 25 day treatment, the herd milk in the tank was analyzed, and practically there were no detectable pathogens. Besides, cow's udders were observed to be healthy. These treatments' results are shown in Table 4 below.

TABLE 4

Bacteriological analysis for each type of treatment

| Tank Bacterial Analysis | Initial Condition, Treatment I (Feb. 19, 2014) | 31-day Cu Treatment (Mar. 22, 2014) | 30-day Cu—Zn Treatment (Apr. 16, 2014) |
|---|---|---|---|
| Total bacteria count | 37,550 | 21,850 | <1,000 |
| Mammary pathogens | | | |
| *Streptococcus Agalactiae* | <100 | <100 | <50 |
| *Staphylococcus aureus* | 500 | 400 | <50 |
| Environmental pathogens | | | |
| *Streptococcus* spp. | <100 | <100 | Not detected |
| *Streptococcus bovis* | <100 | <100 | Not detected |
| *Streptococcus Dysagalactiae* | 450 | <100 | Not detected |
| *Streptococcus uberis* | 5,500 | 2,800 | <50 |
| *Escherichia coli* | 750 | 160 | Not detected |
| Total coliform bacteria | 4,400 | 3,350 | <10 |
| Negative staphylococcus Coagulasa | 3,800 | 2,700 | <400 |
| Others | | | |
| Somatic cell count | 197,000 | 172,000 | 120,000 |

As it may be appreciated, the invention composition eliminated bacterial infections and environmental pathogens in the milk and, therefore, somatic cells also decreased significantly in the said milk. It is necessary to highlight that at 0 time, the initial condition, this was not a herd with no treatment at all, but we have already indicated that a commercial, iodine-base compound was being applied to cover the udders with, and, as shown in the analysis, many infections and pathogens on the udders were transferred to the milk. The first, 31-day treatment with the copper-base compound was able to decrease total bacteria in milk in 41.8% which, although it is very good, is not enough, while the invention composition based on copper and zinc decreased total bacteria below the detection limit.

Example 4: Determination of Prevalence of Bacterial Strains

A total of 386 milk samples of bovines with mastitis were analyzed from two geographical regions of Chile. A total of 363 strains were isolated with different prevalence according to the origin of samples and the severity classification of bovine mastitis (subclinical or clinical). *S. aureus* (30%) was the most frequent in the south where production is based on grass.

The animals analyzed are subject to previous disinfection using iodine as sealant before milking. The samples for the isolation and identification of the bacterial microbiota were centrifuged at 3,000 rpm for 5 minutes and sown on plates with selective and enriching medium as McConkey agar and agar from sheep blood at 5% under aerobic and anaerobic atmosphere in order to support the good growth of most facultative anaerobes, aerobes and microaerophilic bacteria. After incubation, the suspected colonies were recultivated in selective media after Gram staining. According to these results, the bacteria were subject to biochemical analysis as API 20 C AUX (Biomerieux), API 20E (Biomerieux), API Coryne (Biomerieux) and Crystal Bundesliga (BBL) to confirm the initial microbiological diagnose. All isolated and identified microorganisms were stored at −80° C. until their later use.

The milk samples from the south region with signs of clinical mastitis represented 27% of the total in contrast to the central region, where the samples of clinical mastitis reached 56% of the samples received.

According to the microbiological analysis, 101 (26%) presented negative cultures and from the remaining samples a total of 363 microorganisms were isolated (Table 5). A high diversity of microorganisms was identified, mainly in bovines with subclinical mastitis (FIG. 1).

TABLE 5

Number of milk samples and isolated microorganisms

| | Central Region | Southern Region |
|---|---|---|
| Milk samples | | |
| Clinical mastitis | 63 | 75 |
| Subclinical mastitis | 49 | |
| Isolated microorganisms | | |
| Clinical mastitis | 43 | 93 |
| Subclinical mastitis | 53 | 174 |

In the animals of the central region, the central nervous system and *S. uberis* were the most prevailing agents detected in the samples of subclinical mastitis in 15 (28%) and 9 (17%), respectively. In the animals with clinical mastitis *E. coli* (13, 31%) was the most frequent agent detected and CNS was the second most frequent. *S. dysgalactiae* was identified only in the samples of clinical mastitis in this region.

For the samples taken in the southern region, *S. aureus*, CNS and *S. uberis* were the prevailing bacteria, both in clinical and subclinical mastitis (FIG. 1).

When the bacterial isolated microbiota of clinical mastitis was compared in both geographic regions, the results showed that *E. coli* was identified only in the central region, while *S. aureus* was identified only in the southern region. The isolation frequency of *S. uberis* was greater in the southern region compared with the central region (23% compared with 5%, respectively). In addition, isolates of *Corynebacterium* spp. were identified in samples of subclinical and clinical mastitis with similar frequencies in the two regions.

In the central region, *E. coli* was the prevailing bacterium (31% in clinical mastitis), which is probably related to the cattle confinement system in the region.

Example 5: Determination of the Minimum Inhibitory Concentration for the Composition of the Present Invention After incubating the 386 milk samples of bovines with mastitis in selective media and identifying the colonies through biochemical analysis, all isolates were assessed according to the susceptibility of the composition under the present invention by determining the minimum inhibitory concentration through the agar dilution method. The susceptibility to antibiotics was also determined through the agar diffusion method.

The minimum inhibitory concentration (MIC) was determined through the agar dilution method, applying standard bacteriological methods (CLSI 2012a). This way, agar Mueller Hinton (MH) plates were supplemented with the composition according to the present invention in different concentrations ranging from 0.03 mg/L to 1 mg/L. The one-night cultures were diluted to a concentration of $1 \times 10^6$ cells/ml and 5 µl of them were inoculated in the form of stains with a microplate replicator. Each trial was performed in triplicate. The MIC for the composition according to the present invention was defined as the lowest concentration of the formulation where growth was not noted after one-night incubation at 37° C.

Results showed that most of isolated microorganisms were inhibited with concentrations of 0.13 mg/L (146/363) and 0.25 mg/L (92/363), the rest (32/363) was inhibited with greater concentrations ranging between 0.37 mg/L and 0.5 mg/L of the composition according to the present invention.

Figure 2:
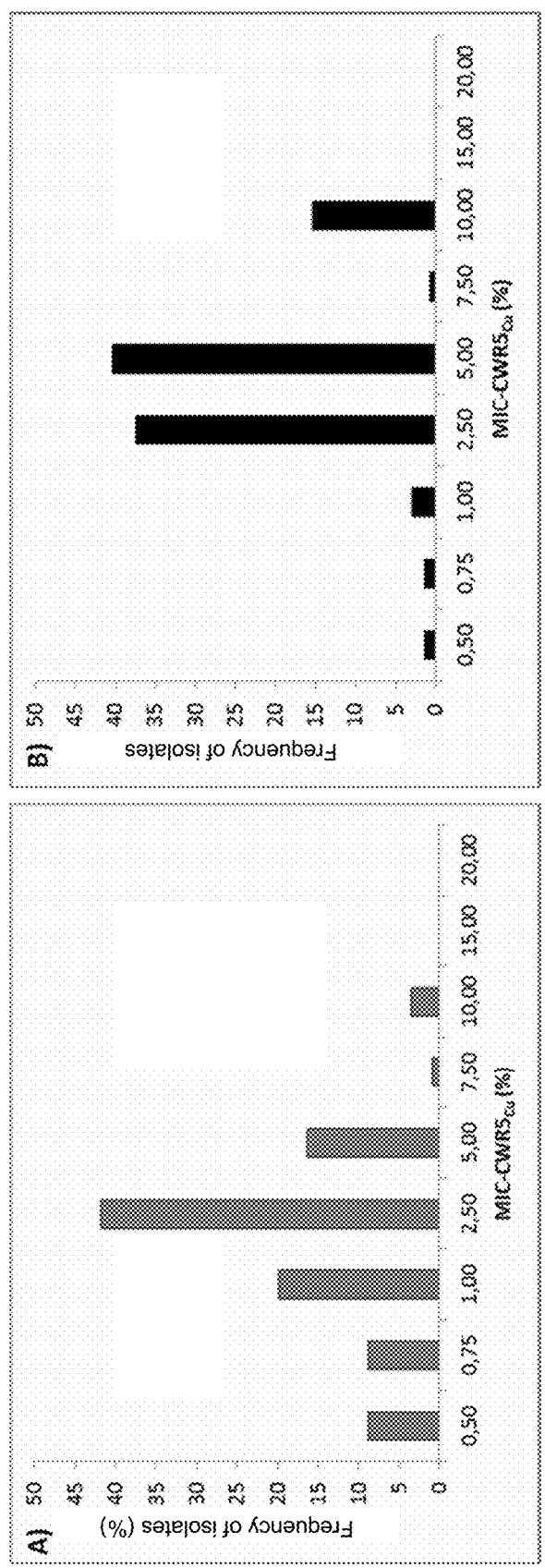
FIG. 2. Frequency of the composition's MIC values according to the present invention for the microorganisms isolated from milk samples with: A) bovine subclinical mastitis (N=227) and B) clinical mastitis (N=136). Each determination was done in triplicate.

The behavior of the species of bacteria apparently has no relation to the origin of the milk samples. A slight different was noted in the frequency of MIC values between the isolates of clinical and subclinical mastitis (FIG. 2). A total of 77 (57%) of isolates with clinical mastitis showed MIC values between 0.25 and 0.5 mg/L of the composition according to the present invention; in contrast, only 47 (21%) of isolates of subclinical mastitis require said range to be eliminated.

Figure 3:
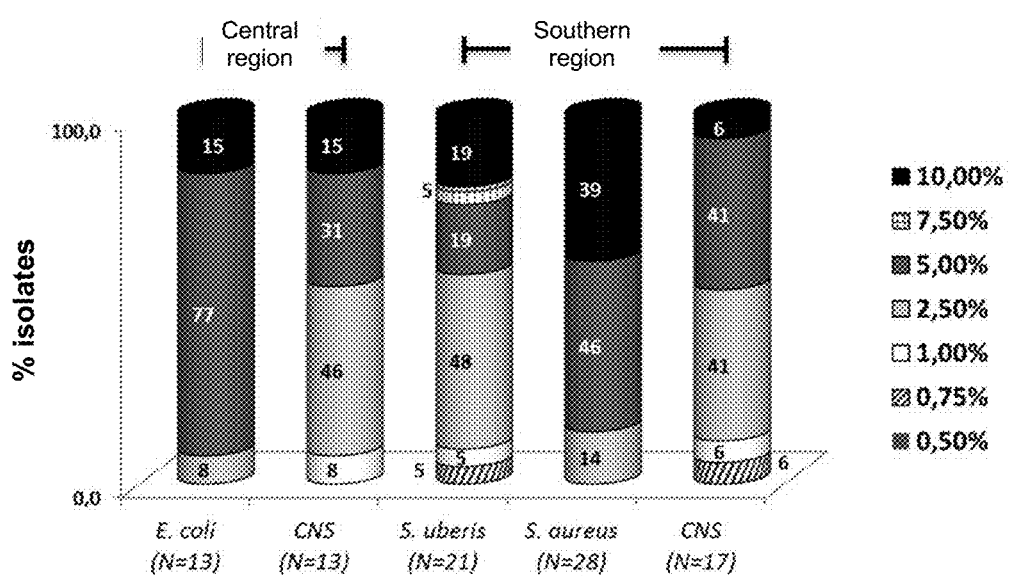
FIG. 3. Frequency of the composition's MIC according to the present invention for the most frequent isolates identified in the clinical bovine mastitis. The subdivision of bars represents the distribution of frequency of MIC values (from 0.25 to 0.5 mg/L) for the different isolations of bovine mastitis.

The distribution of frequencies of MIC values for the isolates most frequently identified in samples of clinical mastitis is shown in FIG. 3. Different strains isolated from clinical mastitis showed variation in a range of 0.37 mg/L to 0.5 mg/L of MIC, where 11 (39%) of *S. aureus* showed higher values of MIC (0.5 mg/L). Over half of CNS and *S. uberis* isolates inhibited with 0.12 mg/L or less of the composition prepared according to the present invention.

Example 6: Sensitivity to Antimicrobial Agents Test

The following antimicrobial agents were assessed (Oxoid Ltd. Hampshire, England):

Amoxicillin/clavulanic acid (AMC),
Trimethropin/sulfamethoxazole (SXT),
Cefotaxime (CTX),
Gentamicin (GN) and
Neomycin (NE).

The bacterial specimens were analyzed according to the Kirby-Bauer disk methodology following the recommendations provided by the guidelines of the Clinical Laboratory Standards Institute (CLSI 2012b) and the BSAC standard (Andrews and Trial 2008).

The microorganisms were incubated in Mueller Hinton agar plates at 35° C. for 18-24 hours in aerobics atmosphere. As quality control *E. coli* (ATCC 25922) and *Staphylococcus aureus* (25923) were used. The CLSI cut-off points were used to interpret the susceptibility of all microbial agents. For the determination of the cut-off point value for neomycin (NE), the BSAC standard was applied.

The resistance pattern against antibiotics showed that 245/363 (67.5%) of isolated microorganisms were simultaneously sensitive to all antibiotics under trial. From these isolates, 81/425 (33%) were of milk samples with clinical mastitis. The isolates of subclinical mastitis showed lower resistance frequencies related to persons with clinical mastitis. In the central region, it was noted that CTX, AMC, Tet and NE antibiotics showed a resistance frequency above 10% in isolates of clinical mastitis. In the southern region, only AMC and Ne meet this condition.

The strains with the highest resistance frequency against antibiotics isolated from clinical mastitis are shown in Table 6. *E. coli*, isolated from the central region, had a variable resistance frequency against different antibiotics tested. In particular 7/13 (54%) of the isolates were resistant to Ne, *S. uberis* isolated from milk samples with clinical mastitis in the southern region showed high frequency of resistance against aminoglycosides GN and Ne (43 and 52%). Some isolates of *S. uberis* were also resistant against CTK (24%). *S. aureus* and CNS isolated from the central and southern regions showed a low frequency of resistance against almost all antibiotics tested.

TABLE 6

Resistance against antimicrobial agents from isolated bacteria wth a higher frequency of clinical bovine mastitis

| | Central Region | | Souterhn Region | | |
| --- | --- | --- | --- | --- | --- |
| | *E. coli* Resistant N° (%) | CNS Resistant N° (%) | *S. aureus* Resistant N° (%) | *S. uberis* Resistant N° (%) | CNS Resistant N° (%) |
| GN | 2 (15.4) | 0 (0.0) | 0 (0.0) | 9 (42.9) | 0 (0.0) |
| CTX | 2 (15.4) | 0 (0.0) | 1 (3.6) | 5 (23.8) | 1 (5.9) |
| AMC | 3 (23.0) | 0 (0.0) | 2 (7.1) | 0 (0.0) | 0 (0.0) |
| TET | 3 (23.0) | 1 (7.7) | 1 (3.6) | 0 (0.0) | 0 (0.0) |
| SXT | 2 (15.4) | 0 (0.0) | 1 (3.6) | 0 (0.0) | 0 (0.0) |
| Ne | 7 (53.8) | 2 (15.4) | 6 (21.4) | 11 (52.4) | 1 (5.9) |

The examples included in this application are of an illustrative character, and they do not limit the scope of the invention protected in the following claims.

The invention claimed is:
1. A biocide formulation for skin protection, comprising as active components:
from 0.05 to 10% pentahydrate copper salts, and
from 0.15 to 10% heptahydrate zinc salts.
2. The biocide formulation according to claim 1, wherein the copper salt is pentahydrate copper sulphate.

3. The biocide formulation according to claim 1, wherein the zinc salt is heptahydrate zinc sulphate.

4. The biocide formulation according to claim 1, wherein the biocide formulation comprises:
from 0.05 to 2% pentahydrate copper salts, and
from 0.15 to 2% heptahydrate zinc salts.

5. The biocide formulation according to claim 1, further comprising at least one selected from the group consisting of a solvent, a viscosity modifier, a humectant, an emollient, a plasticizer, and a colorant.

6. The biocide formulation according to claim 5, wherein the solvent is water or a hydrophilic solvent other than water.

7. The biocide formulation according to claim 5, wherein the viscosity modifier is xanthan gum.

8. The biocide formulation according to claim 6, wherein xanthan gum is present in a concentration from 0.2 to 2% of the biocide formulation.

9. The biocide formulation according to claim 5, wherein the emollient and the humectant are selected from glycerin, sorbitol, propylene glycol, polyethylene glycol, aloe vera, lanolin, and mixtures thereof.

10. The biocide formulation according to claim 5, wherein the emollient and the humectant are present in a concentration between 5 and 30% of the biocide formulation.

11. The biocide formulation according to claim 9, wherein the biocide formulation includes glycerin in a concentration between 5 and 12% of the biocide formulation.

12. The biocide formulation according to claim 9, wherein the biocide formulation includes sorbitol in a concentration between 3 and 10% of the biocide formulation.

13. The biocide formulation according to claim 5, wherein the plasticizer is polyvinyl alcohol.

14. The biocide formulation according to claim 13, wherein polyvinyl alcohol is present in a concentration between 3 to 10% of the biocide formulation.

15. The biocide formulation according to claim 5, wherein the biocide formulation includes an allura colorant which is present in a concentration from 0.01 to 0.5% of the biocide formulation.

16. A biocide formulation for skin protection, the biocide formulation comprises:
from 2 to 10% pentahydrate copper salts, and
from 2 to 10% heptahydrate zinc salts.

17. A method of preparing a medicine for preventing or treating skin infections, comprising providing the biocide formulation according to claim 1.

18. A method of preparing a medicine for covering a teat skin of a milking animal, comprising providing the biocide formulation according to claim 1.

19. A method for treating a teat of a milking animal comprising:
submerging the teat in a biocide formulation after milking,
the biocide formulation comprising as active components:
from 0.01 to 10% pentahydrate copper salts, and
from 0.01 0.15 to 10% heptahydrate zinc salts, and
allowing the biocide formulation to dry on the teat forming a protective film over the teat.

* * * * *